United States Patent [19]

Schneider et al.

[11] Patent Number: 4,498,843
[45] Date of Patent: Feb. 12, 1985

[54] INSULIN INFUSION PUMP

[76] Inventors: Philip H. Schneider, 2939A Cowley Way, San Diego, Calif. 92117; William J. Weber, 520 W. Ellis Ave., Inglewood, Calif. 90302; Thomas A. Massaro, 1339 Hill Top Rd., Charlottesville, Va. 22903

[21] Appl. No.: 404,645

[22] Filed: Aug. 2, 1982

[51] Int. Cl.³ .................. F04B 49/06; B67D 5/48
[52] U.S. Cl. .................................. 417/22; 417/36; 604/65; 604/67; 222/14
[58] Field of Search .............. 224/14, 63; 604/67, 604/65; 128/DIG. 13; 417/12, 22, 18, 36

[56] References Cited

U.S. PATENT DOCUMENTS

| | | | |
|---|---|---|---|
| 3,631,847 | 1/1972 | Hobbs | 604/67 |
| 4,108,575 | 8/1978 | Schal | 417/53 |
| 4,210,138 | 7/1980 | Jess | 128/DIG. 13 |
| 4,231,366 | 11/1980 | Schael | 128/DIG. 13 |
| 4,261,360 | 4/1981 | Perez | 604/67 |
| 4,275,727 | 6/1981 | Keeri-Szanto | 128/DIG. 13 |
| 4,294,248 | 10/1981 | de Fiqueiredo | 604/65 |
| 4,331,262 | 5/1982 | Snyder | 222/14 |
| 4,385,630 | 5/1983 | Gilcher | 604/67 |

Primary Examiner—William L. Freeh
Attorney, Agent, or Firm—Christie, Parker & Hale

[57] ABSTRACT

There is disclosed a microprocessor-controlled peristaltic pump for use in a portable continuous insulin infusion device. The peristaltic pump is configured with a removable cover comprising a part of the pump housing surrounding a pump rotor, and holding a delivery tube between the cover and the rotor. The removable cover combines with a reservoir and the delivery tube to constitute a pre-filled disposable package facilitating installation and removal of the insulin in the device. A microprocessor controls the number of times the rotor turns during a cycle. This operation allows the microprocessor to automatically compensate for different diameter delivery tubes, as well as to allow the physician to vary the on/off time of the pump to administer different dosages.

12 Claims, 7 Drawing Figures

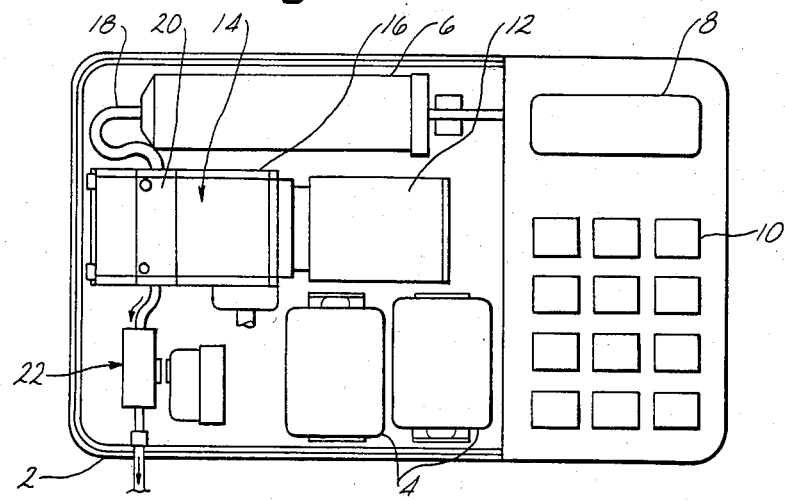
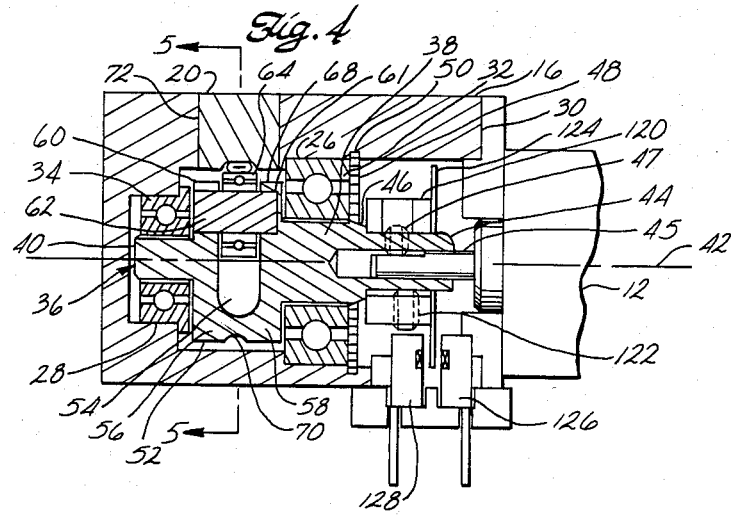

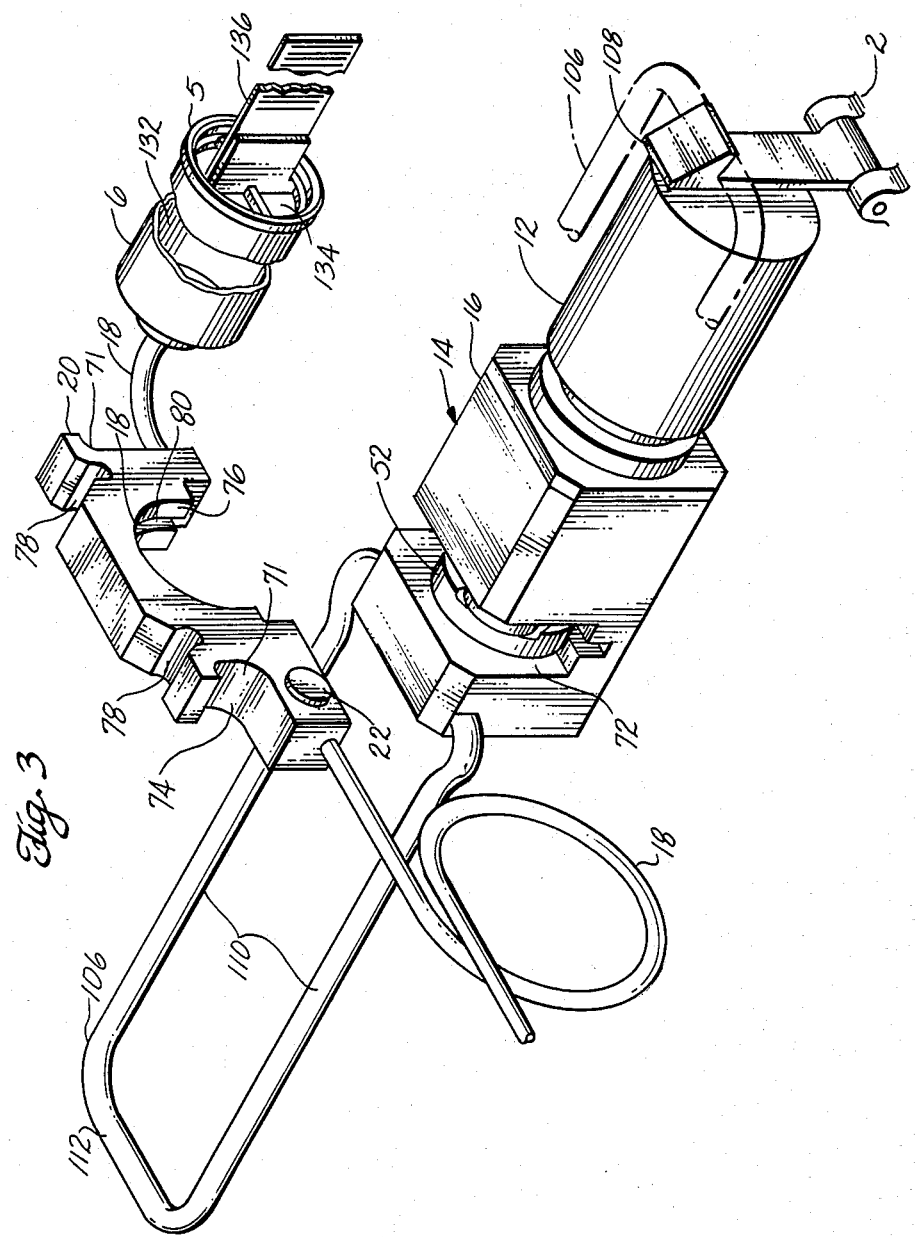

INSULIN INFUSION PUMP

FIELD OF THE INVENTION

This invention relates generally to devices which infuse measured amounts of medication over extended time periods, and specifically to a programmable microprocessor-based portable peristaltic infusion pump for delivery of insulin.

BACKGROUND OF THE INVENTION

In the medical profession, the treatment of diabetes mellitus presents a continuing challenge. Diabetes is a condition characterized by abnormally high blood glucose levels. In human beings, blood glucose is primarily regulated by the pancreas, which secretes insulin. Insulin acts to facilitate the transport of glucose into the cells where it enters into various biochemical reactions.

In diabetes, the transport of glucose is impaired through defects in the function of the pancreas, allowing levels of glucose in the blood to remain high and cellular glucose levels to be markedly reduced.

There are two forms of diabetes. Type I, juvenile onset, or ketosis-prone diabetes is characterized by a reduction in the amount of insulin secreted by the pancreas. In type II, adult, or maturity onset, or ketosis-resistant diabetes, insulin secretion is normal or only minimally depressed, but the biochemical composition of the insulin is such that it facilitates glucose transport less effectively.

Since many of the complications of diabetes are believed to follow directly from the high blood levels of glucose (known as hyperglycemia), much of the clinical effort to treat diabetes has been directed toward improving glucose control by injections of exogeneous insulin.

Of the ten million diabetics in the United States, approximately 15% (all of type I diabetics and a small fraction of type II diabetics) require injections of insulin. Without some form of insulin therapy, type I diabetes is usually a fatal disease.

Glucose levels in the blood are usually dependent upon the amount of food an individual consumes. As the food is metabolized, a portion is converted to glucose and enters the bloodstream. Thus, the glucose level, and the corresponding need for an increased concentration of insulin in the bloodstream to facilitate glucose transport, vary as a function of time.

Conventional insulin therapy consists of one, and sometimes two, subcutaneous injections per day. Unfortunately, this treatment still does not provide adequate control of glucose levels in some individuals with less tolerance for deviations in glucose concentrations. For these individuals the injection of a large dose of insulin once a day increases insulin levels in the blood without any actual correspondence to the immediate concentration of glucose. For such patients there is a need to more carefully match insulin dosages to the actual glucose level in the bloodstream so that the glucose level remains within a narrower, more acceptable range.

This need is satisfied by injecting the same insulin dosage over a longer period of time, to match ambient glucose levels. This slow, constant administration of insulin is known as the baseline or basal dosage. Conversely, there is also a need to administer concentrated doses of insulin just before, or after, meals when glucose levels are highest. The concentrated dosage is known as the bolus dosage.

In developing reliable, continuous insulin infusion systems, two major approaches have been used, closed loop systems and open loop systems.

The closed loop systems typically attempt to mimic the function of the pancreas and deliver dosages of insulin proportionate and in response to augmented levels of glucose in the bloodstream. These devices incorporate a glucose sensor which continually monitors glucose levels in the blood and dispenses insulin to the patient in appropriate doses when the glucose concentration is elevated. "Closed loop" refers to a closed feedback loop which the glucose-sensing equipment forms with the patient and the insulin-dispensing equipment. Unfortunately, engineering problems, especially with the miniaturization of the glucose sensor, have to date precluded the development of a practical closed loop system.

As an alternative to the closed loop system, progress has been made in the development of a reliable open loop system. An open loop system administers dosages of insulin based upon the patient's clinical and dietary history, instead of in response to continuous measurements of glucose level in the blood.

With such a system, the physician usually fixes the basal dosage based upon the patient's previous insulin requirements. The patient usually has relatively free control over the bolus dosage administered at mealtimes. More or less insulin may be taken, depending upon the size of the meal anticipated.

To date the major obstacle to widespread usage of the open loop continuous infusion systems has been the relative unsophistication of portable infusion devices. The devices initially used for clinical studies were not designed for portable use. They were bulky, unattractive, and incorporated very few safety features.

Although much work has been done in the area of portable insulin infusion devices, none incorporates the novel features of the present invention. Typical disclosures of mechanical infusion devices include Kleinman, U.S. Pat. No. 3,964,139; Szabo, U.S. Pat. No. 3,886,938; and Whitney, U.S. Pat. No. 4,269,185. Other types of devices are disclosed by Franetski, U.S. Pat. No. 4,282,872; Blumle, U.S. Pat. No. 3,498,228; Haerten, U.S. Pat. No. 4,077,405; Buckles, U.S. Pat. No. 3,895,631; Scarlett, U.S. Pat. No. 4,274,407; Tucker, U.S. Pat. No. 4,193,397; and Ellinwood, U.S. Pat. No. 3,923,060.

Peristaltic pumps using rollers attached to a rotor have been known in the art for some time. The axes of rotation of the rollers are generally parallel to the axis of rotation of the rotor, and the perimeters of the rollers extend beyond the periphery of the rotor. A flexible tube is held around the rotor in contact with the rollers which extend from the rotor. As the rotor turns, two or more rollers alternately squeeze and release the tube as they roll across the tube's exterior surface. The elasticity of the tube walls cause it to expand to its former shape, drawing fluid into the tube behind the roller. When the next roller compresses the tube, the fluid is forced along by the squeezing of the tube, resulting in a pumping action.

Peristaltic pumps are well suited for use in medical infusion systems, because the medication fluid is isolated from direct contact with mechanical parts. This facilitates the delivery of sterile medications to the patient. In addition, such pumps are capable of delivering measured amounts of fluid, since, at every rotation, some multiple of the effective volume of the tube between each pair of rollers is delivered. Examples of such pumps include Gilmore, U.S. Pat. No. 2,668,637; Hunt, U.S. Pat. No. 3,137,240; and Muller, U.S. Pat. No. 3,384,080.

Although the peristaltic pump provides an attractive method of delivering medication to a patent, prior art pumps have not been well adapted to portable applications. The device disclosed by Muller shows a pump which is compact, but which requires extensive disassembly to replace the reservoir and delivery tube.

In applications where a pump is used to deliver medications through subcutaneous injections, it is especially important to maintain the internal areas of the delivery system in a sterile condition. This requires the tubing to be resterilized or replaced after each use. In prior art, such as Muller, the entire unit must be disassembled to remove the reservoir and delivery tubing for sterilization or replacement. If the tubing is reused too often, it will fatigue and lose the resiliency necessary for the pumping action. Additionally, in an insulin infusion system, the insulin tends to crystallize on the internal surfaces of the delivery system, thereby necessitating frequent replacement.

Thus, there has been a need for a peristaltic pump permitting ready replacement of the reservoir and delivery system to take advantage of practical low-cost injection molding technology.

Another problem frequently encountered with prior art peristaltic pumps is the difficulty in maintaining a precisely controlled pumping rate. In medical pumps, there is a need to deliver small quantities of precisely measured, and often highly concentrated, medications, over a long period of time. The injection of concentrated medications at slow pumping rates is much preferable to the injection of less concentrated medication at a faster rate, because the reservoir can be made smaller and therefore lighter. In portable pump applications, this becomes an important concern, where weight and bulk of the unit control the design criteria.

With medical infusion devices of this type, the pumping rate must be closely regulated between certain narrowly defined limits, and the diameter of the delivery tube upon which the rotors act becomes critical. A deviation in the diameter of the delivery tube causes the effective volume in the tubing between the pump rollers to vary. This makes the volume of liquid pumped for each rotation of the rotor different for tubes of different diameters. These differences in pumping rate can cause significant deviations from the desired dosage of highly-concentrated medication. Variations in tubing diameter can occur within normal tolerances for dimensions of mass-produced medical tubing.

Another causes of nonuniform pumping rates occurs as the pump operates over a period of time. The tubing upon which the pump rotor acts slowly loses some of its natural resiliancy upon which the pump depends for its operation. As this happens, the tubing flattens out, decreasing the effective volume of the tubing between the pump rotor rollers, therefore reducing pump displacement. This causes the effective pumping rate for each rotation of the pump motor to be reduced.

Still another cause of reduced pumping rate is the crystalization of insulin or other medication within the delivery tube, which also reduces the effective volume of the tube between the rotor rollers.

SUMMARY OF THE INVENTION

The present invention avoids the limitations of the prior art by providing an open-loop microprocessor-based portable infusion pump which provides precisely-controlled delivery of insulin at all times.

The insulin pump and its control system are packaged in an impact-resistant plastic case similar to those used on pocket calculators.

The basic components of the delivery system include a reservoir; a peristaltic pump with associated electric motor and reduction gear drive; a medication delivery tube coupling the reservoir to the pump and running through the pump to the patient; means to sense the number of rotations of a pump rotor in the pump; means to sense the depletion of the reservoir; and a microprocessor, electrically connected to the pump and reservoir sensing means and the electric motor to insure that the device delivers a precisely measured dosage of medication to the patient.

The pump is comprised of a pump housing rotatably supporting a cylindrical pump rotor. Two roller bearings are rotatably attached to the rotor, the axes of rotation of the roller bearings being parallel to the longitudinal rotation axis of the rotor. The perimeters of the roller bearings extend slightly beyond the perimeter of the rotor. The pump housing additionally has an access slot which exposes a portion of the rotor.

The remainder of the pump comprises an insulin reservoir, a delivery tube which connects the reservoir to the patient through a hypodermic needle, and a removable cover which fits into the access slot in the housing, over the rotor and the delivery tube which is disposed between the cover and the rotor. The delivery tube is squeezed between the cover and the rotor by a spring bail which is attached to the pump housing and holds the cover into the access slot. The spring bail is secured by a bail catch which is also attached to the pump housing.

In operation, the microprocessor causes the electric motor to drive the reduction gear drive coupled to the pump rotor. This causes the rotor to turn in the pump housing. As the rotor turns, the roller bearings roll along the delivery tube, which is clamped between the roller bearings and the cover by the spring bail. The roller bearings squeeze the liquid in the delivery tube forward, thereby driving the liquid from the reservoir to the patient.

In the preferred embodiment, the reservoir, delivery tube, and removable cover are all constructed of plastic, and the delivery tube is affixed to the interior of the cover. Thus, the combination of these elements may be conveniently and inexpensively replaced each time the reservoir is exhausted. Utilization of the disposable combination eliminates the need to re-sterilize the components of the system prior to each use, and the configuration of a removable cover with the pump allows the fresh reservoir to be quickly installed.

As noted above, the prior-art peristaltic pumps include no provision for controlling the rate of delivery of the pump to compensate for manufacturing variations in the diameter of the delivery tube or to compensate for the diminished resiliency of the delivery tube as the rollers continue to compress and release it.

The present invention meets these needs by providing two feedback loops through a microprocessor to precisely control the rate of delivery of insulin through the delivery tube. The microprocessor is electrically connected to two transducers, one attached to the reservoir to measure the depletion of the reservoir, and one attached to the pump rotor to count the number of rotations of the pump rotor.

The transducers are preferably optical sensors of a type having a photodiode closely spaced from a light-emitting diode (LED). Between the two diodes are a pair of collimating slits, aligned with the diodes. When a transparent object is interposed between the slits, the light emitted from the LED exits the first collimating slit, passes through the transparent object, and enters the second collimating slit, illuminating the photodiode. When an opaque object is interposed between the two slits, the light falling on the photodiode from the LED is interrupted.

In addition to the photodiode/LED pair, the reservoir comprises a cylinder and piston arrangement for holding the medication. The piston has an optical scale attached to and extending from the piston between the collimating slits. The optical scale has a series of alternating transparent and opaque lines along its length. As the piston moves into the cylinder, the optical scale moves through the collimating slits, alternately blocking and transmitting the light from the LED to the photodiode. The photodiode is electrically connected to the microprocessor with appropriate circuitry to signal the microprocessor each time another line on the optical scale moves past the collimating slit. The passage of each line past the collimating slits indicates the injection of another increment of medication into the patient. The microprocessor software is constructed to record each signal originating from the photodiode, enabling it to determine the total amount of medication injected as a function of time.

The optical sensor on the pump shaft is set up in much the same way, but with a circular optical disc attached to the pump rotor shaft. The optical disc has a series of alternating opaque and transparent sectors. Another photodiode/LED combination with associated collimating slits surrounds the optical disc mounted on the rotor shaft. As the rotor shaft turns, the photodiode/LED combination records the passage of the alternating opaque and transparent sectors. This is signalled to the microprocessor, which thereby monitors the number of rotations of the pump shaft.

In the preferred embodiment, the microprocessor is programmed to provide a certain ideal basal dosage rate to the patient, which remains constant throughout the day. The device uses a constant-speed, direct-current, ironless core motor to drive the pump. The microprocessor is programmed to periodically turn the electric motor on for a short period of time each hour to cause the pump to deliver the correct basal dosage per hour. The percentage of time the pump is turned on is defined as the duty factor of the pump. The period of time from when the pump is first turned on, until the pump is again turned on after the pump has been turned off, is defined as the duty cycle.

The microprocessor uses the pump sensor to measure the number of rotations the pump rotor makes at a given duty factor during a single duty cycle. The microprocessor uses the reservoir sensor to measure the actual depletion of the reservoir per duty cycle. By dividing the actual reservoir depletion per duty cycle by the number of rotations of the pump rotor per duty cycle, the microprocessor derives the actual displacement of the pump rotation of the rotor. If the delivery tubing has flattened, due to the constant load of the roller bearings on it, the microprocessor can measure the extent by which the displacement per rotor rotation has been reduced and cause the rotor to turn for a longer period of time (i.e., a longer duty factor) during the next duty cycle. This enables the microprocessor to compensate for variations in the volume of the delivery tube between the rollers.

Another attractive feature of the present device is that the duty factor can be readily changed to change the basal dosage, thereby providing the physician the ability to prescribe different doses of insulin for different patients by modifying the software. This is a distinct advantage over many prior-art devices, which require the patient to dilute the insulin to the proper concentration for infusion by a pump designed for a constant delivery rate.

External controls are provided to allow the patient to initiate the delivery of bolus dosages appropriate to the expected intake of food. Additionally, the microprocessor provides the flexibility necessary for fully programmed time-varying basal and bolus dosages if desired.

BRIEF DESCRIPTION OF THE DRAWINGS

FIG. 2 shows a plan view of the infusion mechanism;

FIG. 3 shows a perspective view of the pump and motor components of the peristaltic pump, as well as the replaceable reservoir and delivery system components;

FIG. 4 shows a cross sectional view of the peristaltic pump including the housing, rotor, and gear reduction drive along section 4—4 of FIG. 5;

FIG. 5 shows another cross sectional view of the peristaltic pump taken along line 5—5 of FIG. 4;

DETAILED DESCRIPTION

Figure 1:
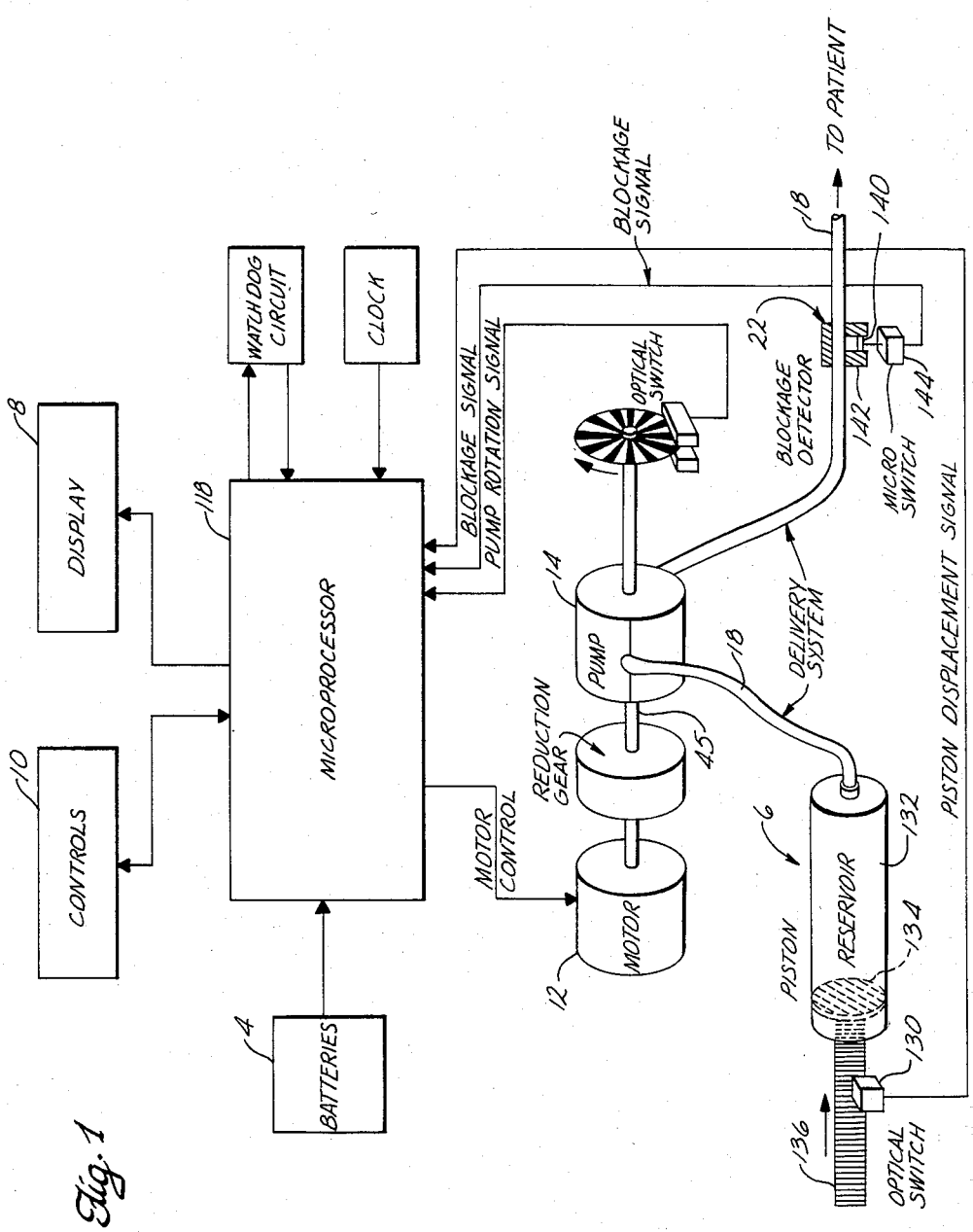
FIG. 1 shows a block diagram of the control system for the microprocessor controlled peristaltic pump.

Referring first to FIG. 2, housing 2 supports the working parts of the insulin infusion device. Housing 2 has external controls 10 to permit the patient to program an onboard microprocessor controlling the rate of injection of insulin. A digital readout 8 is built into the housing to facilitate programming of the microprocessor, and to provide the user with signals indicating any malfunctions of the device. Contained within the housing 2 are a medication reservoir 6, a medication delivery tube 18, a miniature peristaltic pump 14, a miniature electric motor 12 with a gear reduction drive to run pump 14, and batteries 4 to power electric motor 12 and the microprocessor.

In a preferred embodiment, delivery tube 18 runs from reservoir 6 to a pump housing 16 under a removable cover 20 to which the tube is attached. Tube 18 leaves the opposite side of pump housing 16 and then leaves waterproof housing 2 after passing an overpressure or blockage sensor 22 to which the tube is connected. Tube 18 is then connected to the patient with a hypodermic needle (not shown). Housing 2 is sealed by an outer jacket or cover (not shown) which makes a slip fit over the housing.

FIGS. 3, 4, and 5 show the details of peristaltic pump 14. FIG. 3 shows the exterior of pump housing 16, shown in cross section in FIG. 4. Pump housing 16 is formed with first and second bearing seats 26 and 28 of decreasing diameters, enabling a pump rotor assembly (described below) to be installed into the housing from an opening 30 in the end of housing 16 which mounts electric motor 12 and associated gear reduction drive. First and second bearing seats 26 and 28 support first and second rotor bearings 32 and 34. The rotor bearings rotatably support rotor shafts 38 and 40 of a pump rotor 36. The first and second rotor bearings allow rotor 36 to turn freely about its longitudinal rotation axis 42.

Extending from pump rotor shaft 38 is a shaft extension 44 having a diameter less than the diameter of rotor shaft 38. Between rotor shaft 38 and shaft extension 44 is a shaft shoulder 46. A lock ring 48 fits around the shaft extension and into an annular groove 50 in pump housing 16. The lock ring bears on shoulder 46 holding pump rotor 36 and bearings 32 and 34 into pump housing 16. Pump shaft extension 44 is attached to a gear-reduction drive shaft 45 with a set screw 47. Drive shaft 45 is coupled to an electric motor.

Figure 6:
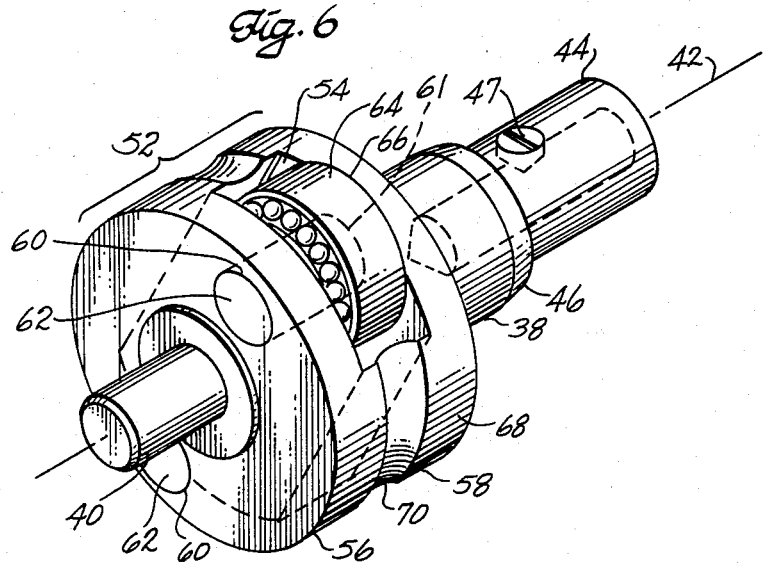
FIG. 6 shows a perspective view of the pump rotor removed from the pump housing.

A central cylindrical section 52 of rotor 36 has a rectangular opening 54 running entirely through the central section 52 perpendicular to rotation axis 42 of the rotor as shown in FIG. 6. The rectangular opening divides central section 52 into two halves 56 and 58. The first half 56 contains two roller axle holes 60 parallel to longitudinal axis 42. The second half 58 contains two axle-receiving holes 61 opposite to and coaxial with the two roller axle holes 60. First and second roller axles 62 are inserted into rotor 36 through roller axle holes 60 and into axle-receiving holes 61.

Each of the roller axles 62 rotatably supports a precision roller bearing 64 in rectangular opening 54. Roller bearings 64 are chosen such that the peripheries 66 of the roller bearings 64 extend beyond the periphery 68 of rotor 36. Central cylindrical section 52 of rotor 36 additionally has a groove 70 which runs around the rotor between roller bearings 64.

Pump housing 16, as described above, also includes an access slot 72 (FIG. 3) which exposes a portion of central cylindrical section 52 of rotor 36. Removable cover 20 is shaped to fit into access slot 72 to surround the portion of central cylindrical section 52 exposed by the access slot. As shown in FIG. 4, cover 20 surrounds a substantial portion (preferably more than 50%) of rotor 36.

Cover 20 has an exterior surface 74 and an arcuate-shaped interior surface 76. Two cover indentations 78 are located on the uppermost portion of the cover exterior surface. The cover has a groove 80 which runs along interior surface 76. Two holes 100 and 102 (FIG. 5), located in the lower portion of cover 20, lead from exterior surface 74 of the cover into the interior surface 76.

Medication delivery tube 18 is led into the interior of cover 20 through first hole 100, around arcuate interior surface 76 of the cover in groove 80, and out of the cover through second hole 102. In the preferred embodiment, tube 18 is affixed in groove 80 along interior surface 76 of the cover, and an anti-migration sleeve 104 (FIG. 5) is affixed to the delivery tube 18 outside the first hole 100.

As best seen in FIGS. 3 and 5, cover 20 may be slidably installed in access slot 72. The cover and access slot, as shown in FIG. 3, have parallel sides, but alternatively the cover and access slot can be tapered to facilitate installation of the cover in the slot. A latch formed by a spring bail 106 is rotatably mounted at one end of the pump housing 16. A bail catch 108 is pivotally coupled to external housing 2 at the opposite end of the pump housing to hold bail 106 over cover 20 and urge the cover into access slot 72.

Spring bail 106 is comprised of two parallel longitudinal members 110 coupled by a single shorter end member 112. The lengths of the longitudinal members 110 are chosen such that end member 112 engages with bail catch 108. When bail 106 contacts cover 20, longitudinal members 110 seat in cover indentations 78 on the upper portion of exterior surface 74 of the cover. As shown in FIG. 3, the cover can be molded with depressions 71 on either side of the exterior surface of the cover to provide gripping surfaces facilitating installation and removal of the cover in access slot 72.

Figure 7:
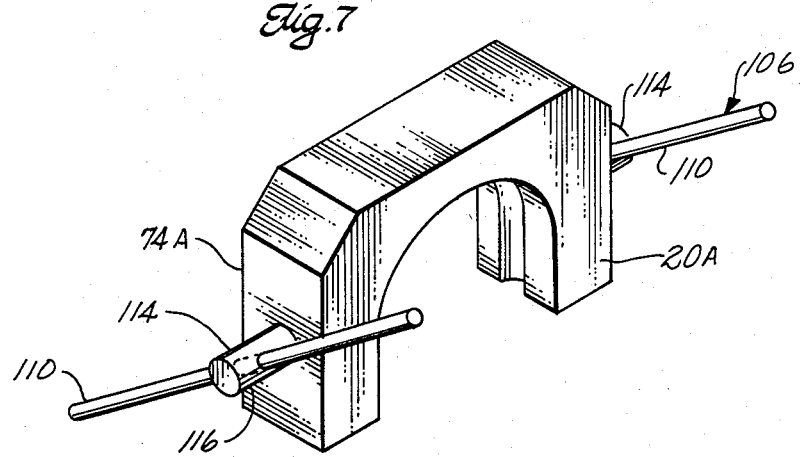
FIG. 7 shows an alternate embodiment of the removable cover.

In an alternative embodiment shown in FIG. 7, two bail pins 114 extend from opposite sides of the exterior surface 74 of a cover 20A. The pins each have a hole 116 through the portion protruding from the external surface 74A of the cover. Bail longitudinal members 110 run through the holes 116, thereby attaching the cover 20A to bail 106. In this embodiment, cover 20A is included as a permanent part of pump housing 16. Instead of being threaded into the interior of the cover 20A through holes in the cover, delivery tube 18 is simply laid across rotor 36 and clamped into position with bail 106.

In operation, the assembly of cover 20 and delivery tube 18 is inserted into access slot 72. Spring bail 106 is then engaged with bail catch 108 to force cover 20 over the central section of rotor 52. The delivery tube is thereby squeezed between the cover and roller bearings 64. No other part of rotor 36 contacts tube 18 because the tube is sheltered in groove 70 which circles the central section of the rotor between the bearings 64.

Roller bearings 64 are aligned with cover groove 80, and also with delivery tube 18 which is seated in the groove. When the drive shaft 45 is driven by the electric motor, rotor 36 turns about its longitudinal axis 42. Bail 106 holds delivery tube 18 between cover 20 and roller bearings 64 with enough force to cause the roller bearings to collapse the flexible delivery tube. As the rotor turns, the roller bearings thus roll along the delivery tube inside cover 20, causing liquid in the tube to be pumped from reservoir 6 to the patient.

In an alternate embodiment, a single roller bearing 64 may be coupled to rotor 36, permitting the diameter of the rotor and the overall dimensions of the pump to be smaller. When only one roller bearing 64 is used, a check valve is installed in delivery tube 18, permitting fluid to flow only from the reservoir to the pump. The check valve is also spring-loaded to prevent a free-flow condition from the reservoir to the patient in the absence of any positive pumping action initiated by the roller acting on the delivery tube.

In the preferred embodiment, delivery tube 18, cover 20, and reservoir 6 are all constructed of plastic, allowing these elements to be sold as a prepackaged, sterile, disposable unit. Reservoir 6 is prefilled with insulin, thereby allowing a patient to install the reservoir, cover, and delivery-tube combination in the device by simply slipping cover 20 into access slot 72 and securing the cover with spring bail 106. The device is attached to the patient through a hypodermic needle connected to the delivery tube.

The device functions as a constant insulin infusion system, operating independently for a period of between three and five days. When prepackaged reservoir 6 is exhausted, the reservoir, delivery tube, cover, and hypodermic-needle combination may be discarded and another low-cost, prefilled insulin reservoir package or cartridge assembly installed in the device.

As noted above, there is often a problem in peristaltic pumps in maintaining a constant rate of delivery at a constant pump-rotor rotation rate. As shown in FIG. 5, at least one of precision roller bearings 64 is constantly in contact with delivery tube 18. Ultimately, the repeated compression and release of the delivery tube by the roller bearings leads to a loss of the natural resiliency of the tube walls. This results in a flattening of the delivery tube.

The peristaltic pump is entirely dependent upon the "memory" in the tube walls to cause the tube to expand after the roller bearing has compressed and passed over the tube. As the tube expands to its former shape, fluid is drawn into the tube behind the roller. When the next roller compresses the tube, the fluid therein is forced along by the squeezing of the tube. Each time a pair of rollers pass by a section of tubing, a volume of fluid is pumped equivalent to the product of the length of the tubing between the rollers and the cross-sectional area of the tubing. Naturally, if the tubing flattens out as the rollers continue to bear on it, the effective volume pumped for each rotation of the rotor will be diminished, causing the pumping efficiency to slowly deteriorate.

Prior-art pumps with constant-speed motors have been uncompensated for this problem. But with concentrated insulin infusions, the problem cannot be ignored, since the health of the patient depends upon the capability of the device to deliver constant amounts of insulin over periods of time sufficient for the delivery tubing to flatten significantly.

The present invention solves the problems of the prior art by providing a microprocessor-controlled peristaltic pump which uses insulin sufficiently concentrated to require the pump to be turned on for only a short period of time each hour. The microprocessor regulates the "on" time of the pump to vary the basal dose per hour, and to compensate for deviations in the diameter of delivery tube 18.

Duty factor is defined as the percentage of time the pump is turned on.

Duty cycle is defined as the length of time beginning from when the pump turns on until the pump next turns on. Thus, with a 1% duty factor and a one-hour duty cycle, the pump would be on for 36 seconds and off for 59 minutes and 24 seconds.

FIG. 1 shows a block diagram of the microprocessor control system. A microprocessor 118 is preferably selected from a family of components which can be directly interconnected, thereby minimizing component count and overall size of the controller. The Motorola 6805 microprocessor is an example of such a device. The microprocessor is electrically connected to the constant-speed electric motor, allowing the microprocessor to turn the motor on or off according to its programming.

To insure delivery of a correct dosage of medication to the patient at a proper rate, a schedule is contained in the microprocessor software specifying basal dosage as prescribed by the physician. Since the motor operates at a constant speed, the rotor rotation speed, as defined by the gear reduction drive, is also fixed. The dosage to the patient is set by defining the length of time the pump is turned on each hour. Stated another way, the duty factor of the pump may be varied to adjust the dose injected per duty cycle.

When the delivery tube flattens out under the influence of constant compression by the roller bearings, a different condition occurs. The displacement of the pump is reduced by the reduction in the volume of the delivery tube between the rollers. This condition causes the pump displacement per rotation of the rotor to be reduced. To permit the pump to displace the same volume of fluid with a flattened delivery tube, the rotor must be turned more times. The microprocessor can compensate for variations in the diameter and displacement of the delivery tube by leaving the pump turned on for a longer period of time each hour. In other words, the duty factor of the pump may be increased to insure that the basal dose per duty cycle remains constant in spite of a diminution of the diameter of the delivery tube.

To adjust the duty factor, the microprocessor measures two quantities, the number of rotations the pump rotor makes per duty cycle, and the depletion of the reservoir per duty cycle. The advantage of using a microprocessor to control the delivery of medication is that the pumping rate is always being monitored so that corrections to the duty factor are made each duty cycle to compensate for flattening of delivery tube 18.

The means by which the microprocessor measures the number of rotations of the pump rotor per duty cycle is illustrated in FIG. 4. As described above, pump shaft extension 44 is attached to gear-reduction drive shaft 45 by set screw 47 located in pump shaft extension 44. A circular collar 120 is attached to shaft extension 44 by means of another set screw 122. Mounted on collar 120 is a circular optical disc 124 having a series of uniformly-spaced, alternating, opaque and transparent sectors aligned in a radial direction, as shown in FIG. 1.

Also located within housing 16 is an optical sensor which comprises a photodiode 126 on one side of optical disc 124 and a light-emitting diode (LED) 128 on the opposite side of the disc. Between the photodiode and the disc, and also between the disc and the LED, are a pair of collimating slits aligned with the diodes.

When a transparent sector on disc 124 is interposed between the slits, the light emitted from LED 128 exits the first collimating slit, passes through disc 124, and enters the second collimating slit, illuminating photodiode 126. The photodiode is electrically connected to the microprocessor so that the presence of the transparent line between the two diodes is recorded as an "on" or "high" signal by the microprocessor. When rotor 36 turns, the next opaque sector is interposed between the two diodes, interrupting the light falling on the photodiode. This condition is recorded by the microprocessor as an "off" or "low" signal.

Software within the microprocessor causes the computer to count the number of on/off pulses coming from photodiode 126 per duty cycle. The microprocessor can count the number of rotations of the pump quite precisely by counting the signals coming from photodiode 126, since the alternating opaque and transparent sectors on the disc are uniformly spaced.

The use of the optical sensor attached to the rotor shaft enables the delivery of fluid to be measured quite accurately. Using tubing with an inside diameter of 0.020 inch, it is estimated that the pump will displace 0.0092 milliliters, or 0.9 units, of insulin per full revolution of the rotor. Using thirty sectors on the disc, the controller can determine when each 0.03 units of insulin has been infused and can regulate accumulated dosage with this precision.

The means by which the microprocessor measures the depletion of reservoir 6 per duty cycle is similar to the method used to count the number of rotations of pump rotor 36 per duty cycle. A photodiode/LED pair 130 coupled to the microprocessor is used to signal the incremental depletion of reservoir 6. Again, collimating slits are disposed between photodiode/LED pair 130 to collimate the light falling on the photodiode from the LED.

Reservoir 6, as shown in FIG. 1, comprises a cylinder 132 with a piston 134 slidably disposed therein. Attached to piston 134 and extending out from it is an optical scale 136 having alternating opaque and transparent lines along its length. Like optical disc 124 described above, optical scale 136 extends between photodiode/LED pair 130. When piston 134 moves into cylinder 132 as reservoir 6 depletes, optical scale 136 moves through the collimating slits, alternately blocking and transmitting the light traveling from the LED to the photodiode.

The photodiode adjacent optical scale 136 is electrically connected to the microprocessor. As the reservoir is depleted, the microprocessor receives a series of on/off signals from the photodiode next to the optical scale, depending upon whether a transparent or an opaque line is adjacent the collimating slit.

Once the quantities specified are measured, the microprocessor can regulate the delivery rate of the pump. The microprocessor sets the duty factor of the pump and causes the pump to go through a duty cycle, turning the motor on for a period of time, and then turning it off.

Using the reservoir-depletion sensor means, the microprocessor measures the actual depletion of the reservoir per duty cycle. The microprocessor also counts and records the number of rotations of the pump rotor completed in the given duty cycle to effect the measured depletion of the reservoir. Using these two quantities, the microprocessor determines the exact displacement of the pump per rotation of the rotor for each duty cycle. If the delivery tube is flattened, and the displacement of the pump per rotation is diminished, software in the microprocessor causes the rotor to turn more often in each duty cycle (i.e., increase the duty factor), thereby compensating for the flattening of the tube and delivering a constant volume in each successive duty cycle.

This process is particularly well adapted to use with miniature peristaltic pumps wherein the pumping efficiency of the pump may diminish due to loss of the resiliency of the delivery tube under the roller bearings. In spite of the fact that the pumping efficiency of a peristaltic pump diminishes, the microprocessor measures the actual depletion of the reservoir and, therefore, the actual dosage for every duty cycle. This allows the microprocessor controllably to correct the duty factor of the pump during every duty cycle to compensate for loss of elasticity in the delivery tube walls.

If the pump delivers less fluid per rotation of the pump rotor within a given period of time, the microprocessor can increase the "on" time or duty factor of the pump to deliver a constant volume of fluid each duty cycle.

Additionally, the use of a microprocessor to control the duty factor of the pump allows the pump to be individually programmed to suit each patient. The insulin requirements of different diabetics vary, such that insulin in a device with a continuous constant rate of infusion must be diluted to the proper concentration so that the dose per unit time is correct. With the instant device, the physician can vary the prescription by reprogramming the microprocessor for a different duty factor. A special code can be provided in the software which allows only the physician to reprogram the device for the prescribed basal dosage. External controls accessible to the patient are provided to allow the patient to initiate a bolus dosage appropriate to the expected intake of food.

Another advantage of using a microprocessor lies in the fact that the software can be designed to measure the accumulated dose over periods of hours. If, through accident or mistake, the patient attempts to initiate too many bolus doses within too short a period of time, the microprocessor will terminate pump operation before the pump exceeds limits set by the physician in the software. Other features in the software enable the microprocessor to actuate an audible alarm connected to the microprocessor in the event of such an overdose condition, as well as display a message on a digital display connected to the microprocessor, to inform the user of the problem.

The utilization of a microprocessor with the present design also facilitates the incorporation of several features which would not otherwise be available in pump controller systems. One such feature is the inclusion of an overpressure blockage detector 22 to signal the user of blockage in the hypodermic needle or the delivery tube 18 between the hypodermic needle and the peristaltic pump.

As depicted in FIG. 1, the sensor 22 constitutes a high-friction sensor piston 140 disposed in a sensor cylinder 142 in communication with the delivery tube. In the preferred embodiment, the piston and cylinder arrangement are integrally molded into removable cover 20 as shown in FIG. 3. Alternately, the overpressure sensor may be enclosed within external housing 2 as a separate component as shown in FIG. 2.

When an overpressure condition exists in delivery tube 8 due to blockage, the piston moves out of the sensor cylinder and actuates a microswitch 144 which is disposed adjacent the cylinder. The microswitch is electrically connected to the microprocessor. When the microprocessor receives a blockage signal from the microswitch, it implements programmed instructions contained in its memory and actuates the audible alarm. An error message may also be displayed on the digital display. Other types of overpressure sensors (such as diaphragm-actuated switches or other pressure transducers) may be used to generate a blockage signal to the micropressor.

Use of the microprocessor also allows an audible alarm and an error message to be displayed by the LED readout in the event of low batteries, failure of the pump to turn as commanded, failure of the pump to turn as fast as is required, insulin dosage exceeding predetermined limits over defined periods of time, continuation of pump operation beyond the required period, and blockage in the delivery tube between the reservoir and the pump.

The inclusion of these numerous safety features is facilitated by the feedback loops from both the reservoir and the rotor. The flexibility provided by the programmability of the microprocessor allows the physician to program built-in safeguards, preventing elderly or feeble patients from using the device incorrectly.

What is claimed is:

1. A microprocessor controlled peristaltic pump comprising:
   a pump having a rotatable pump rotor, and a pump switch means coupled to the pump rotor which alternately opens and closes as the pump rotor rotates;
   a motor coupled to and driving the pump rotor;
   a reservoir having a cylinder, and a piston which moves into the cylinder as the reservoir is depleted;
   a delivery tube connecting the reservoir to the pump, running through the pump, over the rotor, and thence to a delivery site;
   a reservoir switch means coupled to the piston which alternately opens and closes as the reservoir is depleted; and
   a microprocessor electrically connected to the pump switch means, the reservoir switch means, and the motor such that the microprocessor programmably controls the number of revolutions the pump rotor makes per unit of time in response to signals received from the pump switch and the reservoir switch.

2. The device of claim 1 wherein the pump switch means comprises:
   an optical disc coupled to the pump rotor and having alternatingly opaque and transparent radially aligned sectors; and
   an optical sensing means adjacent the disc such that as the rotor rotates, the optical sensing means registers the presence of an opaque or transparent sector on the optical disc adjacent the optical sensing means.

3. The device of claim 2 further comprising:
   a pump shaft extending from the pump rotor;
   an annular collar affixed to the optical disc; and
   the collar being mounted on the pump shaft and affixed thereto with a set screw in the collar.

4. The device of claim 2 wherein the optical sensing means comprises:
   a photodiode on one side of the optical disc; and
   a light emitting diode on the opposite side of the optical disc.

5. The device of claim 4 wherein the optical sensing means further comprises:
   a first light collimating slit interposed between the photodiode and the optical disc; and
   a second light collimating slit interposed between the light emitting diode and the optical disc.

6. The device of claim 1 wherein the reservoir switch means comprises:
   an optical scale attached to and extending out from the piston and having alternating opaque and transparent parallel lines; and
   an optical sensing means adjacent the optical scale such that the optical sensing means registers the presence of an opaque or transparent line on the optical scale adjacent the optical sensing means.

7. The device of claim 6 wherein the optical sensing means comprises:
   a photodiode on one side of the optical scale; and
   a light emitting diode on the opposite side of the optical scale.

8. The device of claim 7 wherein the optical sensing means further comprises:
   a first light collimating slit interposed between the photodiode and the optical scale; and
   a second light collimating slit interposed between the light emitting diode and the optical scale.

9. The device of claim 1 further comprising a digital readout connected to the microprocessor.

10. The device of claim 1 further comprising an overpressure sensor means coupled to the delivery tube downstream of the pump rotor and electrically connected to the microprocessor such that an overpressure condition in the delivery tube downstream of the pump rotor causes the overpressure sensor to send a signal to the microprocessor.

11. The device of claim 10 wherein the overpressure means comprises:
    sensor cylinder having a first end in communication with the delivery tube and a second open end;
    a fluid sealed sensor piston in the sensor cylinder; and
    a microswitch connected to the microprocessor and adjacent the second end of the sensor cylinder such that when an overpressure condition exists in the delivery tube, the piston is forced out of the cylinder actuating the microswitch.

12. The device of claims 1 and 10 further comprising an audible alarm connected to the microprocessor which may be programmably actuated by the microprocessor.

* * * * *